(12) United States Patent
Bergersen (10) Patent No.: US 11,369,458 B1
(45) Date of Patent: Jun. 28, 2022

(54) METHOD AND DEVICE TO INCREASE BLOOD CIRCULATION AND TO ENCOURAGE TOOTH ERUPTION AND MUSCLE EFFICIENCY OF A DENTAL PATIENT

(71) Applicant: ORTHO-TAIN, INC., Toa Alta, PR (US)

(72) Inventor: Earl O. Bergersen, Glenview, IL (US)

(73) Assignee: ORTHO-TAIN, INC., Toa Alta, PR (US)

( * ) Notice: Subject to any disclaimer, the term of this patent is extended or adjusted under 35 U.S.C. 154(b) by 0 days.

(21) Appl. No.: 17/405,337

(22) Filed: Aug. 18, 2021

(51) Int. Cl.
*A61C 7/08* (2006.01)
*A61C 7/00* (2006.01)

(52) U.S. Cl.
CPC ............... *A61C 7/08* (2013.01); *A61C 7/008* (2013.01)

(58) Field of Classification Search
CPC .................................. A61C 7/08; A61C 7/008
See application file for complete search history.

(56) References Cited

U.S. PATENT DOCUMENTS

| | | | |
|---|---|---|---|
| 3,898,736 A | 8/1975 | Bergersen | |
| 4,799,884 A | 1/1989 | Bergersen | |
| 5,645,420 A | 7/1997 | Bergersen | |
| 6,626,664 B1 | 9/2003 | Bergersen | |
| 7,234,933 B2 | 6/2007 | Bergersen | |
| 9,393,083 B2 | 7/2016 | Bergersen | |
| 9,517,113 B2 | 12/2016 | Bergersen | |
| 10,537,407 B2 | 12/2020 | Bergersen | |
| 10,874,593 B2 | 12/2020 | Bergersen | |
| 10,980,615 B2 | 4/2021 | Bergersen | |
| 2014/0272761 A1* | 9/2014 | Lowe | A61C 17/22 433/24 |
| 2015/0079533 A1* | 3/2015 | Lowe | A61C 7/08 433/24 |
| 2017/0304024 A1* | 10/2017 | Nobrega | A61C 7/08 |
| 2018/0153733 A1* | 6/2018 | Kuo | A61F 5/58 |
| 2020/0315745 A1* | 10/2020 | Way | A61C 19/02 |
| 2021/0100723 A1 | 4/2021 | Bergersen | |

\* cited by examiner

*Primary Examiner* — Heidi M Eide
*Assistant Examiner* — Drews S Folgmann
(74) *Attorney, Agent, or Firm* — Taft Stettinius & Hollister LLP; Joseph M. Bennett-Paris (57) ABSTRACT

A device including one or more preformed or customized eruption guidance appliances placed in an individual's mouth. The preformed appliances are vibrated with a pulsation device to encourage tooth eruption by increasing the force and efficiency of the eruption toward a preferred location and a preferred alignment as well as providing increased blood flow and blood oxygen flow to the muscles and tissues in and around the oral cavity of the individual. The preformed guidance appliance driven by the pulsation device is selected from a range of guidance appliances, each of which is selected by size and shape to fit an individual based on the individuals anticipated tooth and jaw size as well as the growth profile. The pulsation can increase the blood and oxygen flow to the many muscles that surround the appliances outside surfaces that can alter mouth breathing, prevent impingement of the oropharynx from the abnormal distalization of the tongue and mandible during sleep, the proper resting posture of the tongue, increased nasal breathing, prevent snoring, improve abnormal swallowing, correct thumb sucking and various abnormalities of speech.

5 Claims, 5 Drawing Sheets

METHOD AND DEVICE TO INCREASE BLOOD CIRCULATION AND TO ENCOURAGE TOOTH ERUPTION AND MUSCLE EFFICIENCY OF A DENTAL PATIENT

TECHNICAL FIELD

The present disclosure relates to a method and device for aligning the teeth of both children and adults, and more particularly relates to a device coupled to an oral appliance to encourage and intensify the eruption of erupting teeth and increase muscle efficiency by increasing the blood circulation, oxygen and growth to a preferred location and preferred alignment and a method therefore.

BACKGROUND OF THE DISCLOSURE

The statements in this section merely provide background information related to the present disclosure and should not be construed as constituting prior art.

Various appliances have been developed to guide erupting teeth into preformed tooth sockets in order to line them up properly and as a result, to improve a child's occlusion. In order to accomplish this, it is necessary to predict the sizes and shapes of the incoming teeth (usually the permanent teeth, but also in some cases the deciduous teeth).

The permanent incisors do not usually erupt directly into the proper place to prevent a malocclusion to obtain perfectly aligned teeth. The lower permanent incisors usually erupt lingual to the crowns of the deciduous incisors they replace. These incisors are often not able to become properly positioned labially into an ideal alignment, which results in the development of a crowding of these front teeth. This undesirable positioning is particularly seen when the permanent lateral incisors and canines erupt. Once the permanent central incisors (upper and lower) erupt and since these incisors are usually the first ones to erupt, such incisors usually easily make room for themselves by taking away some of the space needed for the lateral incisors to erupt in a straight and upward direction into the individuals upper and lower arches.

The upper incisors usually erupt labially to the deciduous incisors and often experience the same problem which also results in crowding in a similar but usually less severe way for the laterals and canines. When the permanent incisors are guided into the arch by forcing themselves into predetermined sockets, called eruption guidance, their forceful eruption widens the arch by producing no crowding prior to collagenous fiber development that serves to stabilize the teeth into their straightened result after the straightening has taken place.

If the teeth could be directed to erupt more rapidly with more eruptive force, the more rapid and more forceful eruption could encourage these erupting permanent incisors to more forcibly push their way into the deciduous arch, that is almost always considerably smaller than the permanent arch into which the permanent incisors are intended to increase into a larger arch which results in straight permanent anterior teeth. This does not happen as frequently in the upper arch as the lower, hence, the higher percentage of lower incisor crowding exceeding 50% (mean 53%) and can be as high as 80% in the mandibular anteriors while the maxillary crowding is 27%.

What is needed therefore is a device that assists the eruption of teeth in moving the teeth toward a preferred alignment more rapidly.

The present invention is intended to improve upon and resolve some of these known deficiencies of the art.

SUMMARY OF THE DISCLOSURE

It has been the experience of the inventor that biting and clenching the teeth tends to increase the speed and strength of tooth eruption when standard fixed orthodontics is performed after exercising two (2) hours per day. Such cases had a shortened period of treatment, being 50-75% faster than if the exercises were not performed. While not the result of a clinical study, this result is likely due to the increase in blood circulation around these teeth which seems to persist for at least a year after the clenching stopped.

As a result of these observations, it is possible to speed up and strengthen the eruption force of erupting teeth with the introduction of a vibrating or pulsating force that can increase the total eruption speed and force of these erupting teeth. An increase in strength and speed of eruption can increase the ability of the erupting permanent teeth to make more room for themselves due to the eruption force and as a result produce larger increases in arch size. The vibrating force results in a mean of about 4 mm (lower arch widening) and about 5 mm (upper arch widening) which not only increases the result but also increases the speed of the changes.

Vibrating or pulsating effects in nature and when applied to the human have been observed and used for generations. Foot massage devices with vibration have been used to ease foot tiredness and discomfort. Also, vibration instruments have been used to relieve pain for muscle aches and injuries. In dentistry, vibration machines have been used to more easily mix plaster of Paris for model making and when filling impressions of teeth. Vibration from such a machine pouring plaster into an impression makes the plaster flow like water to thereby produce better casts of teeth.

A similar vibration of the earth from the effects of an earthquake produces a state called liquefaction. Liquefaction is particularly apparent when experienced by a sandy and wet foundation base for a home. The liquefaction causes a major settling and sinking into the earth and is an important factor to assess when buying a home in an earthquake area. The application of vibration applied by a pulsation device and transmitted or applied to an eruption guidance type of appliance that has preformed predicted tooth sockets can be a very beneficial way to improve the natural widening of a dental arch and a natural way to increase arch space for potentially larger permanent teeth and more crowded erupted teeth. As a result of a more efficient forceful and rapid way of eruption guidance provides a great advantage.

For many years there have been products that increase muscular efficiency, strength, endurance and healing as well as to reduce pain through vibration. The clenching and relaxing protocol of eruption guidance orthodontic treatment increases the blood circulation and increases the warmth of tissues. Any time there is an increase in blood circulation there is an increase in oxygen which is a vital ingredient for growth and healing of injuries. Massaging muscles induce the brain to release oxytocin and reduce ACTH and Beta endorphins which heals pain and increases muscular efficiency. A few examples can illustrate these principles. It was found that patients that wore these eruption guidance appliances (C, IG, G) as well as the adult N appliances found that after wearing one of these appliances (N series) weight lifting increased by 10%, a long-distance runner made sure the G appliance was worn the night before a track meet and it increased his running speed the next day. In a study of mandibular advancement compared to a control sample, the treated cases had 52% more condylar growth of the lower jaw over the control sample. This increase in growth is probably due to increased blood oxygen. Similar examples of identical twins, one with abnormal sleep issues while using an eruption guidance appliance had increased growth in height, catching up to the height of the taller normal twin. Massaging muscles can decrease pain and increase function of muscles as well.

To combine vibration with sleep, speech and habit correction appliances (called the Habit Correctors) is to be able to increase oxygen to not only the dentition and its supporting soft tissue and bone with vibrations has a direct effect on the speed of tooth movement, but also to the various muscles of the oral cavity. This is possibly due to the contact of the appliance with the muscles surrounding the appliance namely the masseters, tongue muscles, and the orbicularis oris around the lips. It helps when the patient is using the vibration with the appliance in the mouth and have the patient squeeze all of the muscles against the outer margins of the appliance. This ensures that the muscles are well vibrated at the same time as the teeth, and stimulate the blood flow and the oxygen to both muscles and dentition.

This procedure can significantly aid in several areas in treatment of sleep problems and habits that often contribute to the presence of sleep issues. Speech is also affected particularly by the tongue and lips. The strengthening of these muscles with increased oxygen can be valuable in aiding several issues. One main issue are oral habits that can have a direct effect on normal sleep. These involve mouth breathing which is directly related to the strength and length of the lips in developing closed lips in sleeping. The treatment often involves some daytime wear with the patient actively closing the lips over the front area of the habit corrector. Any increase in the strength of the muscles accentuated with the increase of blood flow, oxygen and possible hormones. In the stimulation of growth that can aid in the length of the lips.

Strengthening of the tongue with increased blood flow and oxygen can help with both the widening of the upper posterior arch since the tongue is forced to be elevated in its resting posture within the palate and positioning tongue in proper resting position in the palate of the mouth. This Habit Corrector appliance has palatal buttons, see FIG. 6, element number 93, that the patient is instructed to forcefully widen using the tongue with lateral pressure to increase the palatal width and increase normal nasal breathing. This strengthening of the tongue by use of the vibrating device aids in this widening as a result in the increased blood flow and oxygen level in the tongue muscles that in turn aid in normal nasal breathing as well as preventing mouth breathing.

Mouth breathing at night is the major factor in its adverse effect on neurocognitive and behavior symptoms as a result of the constriction of the oropharynx. This lack of incoming air into the lungs has a direct effect of the brain, immune and endocrine systems in the body. When the tongue positions itself in the palate instead of an established habit of positioning it within the mandibular body, mouth breathing becomes impossible and as a result increases normal nasal breathing. This elevated tongue position also prevents the tendency for nighttime mouth breathing which also prevents the base of the tongue to be displaced and in contact against the anterior wall of the oropharynx which exerts pressure on the airway and can close the airway either partially or entirely.

The various problems involving sleep and habits, in particularly, the establishment of normal nasal breathing with the elimination of mouth breathing by developing normal lip closure at rest while breathing during the day or night but especially at night is beneficial in creating normal nasal breathing. When a person sleeps, if the lips stay closed and the mandible for the most part resists slipping distally as the muscles relax, the following muscles have a direct impact:

1. Masseter muscle which functions for jaw closure and resists its opening
2. Internal pterygoid which is attached to the tuberosity and neck of the mandible aids in keeping the mandible from slipping distally.
3. External pterygoid muscle which also aids in keeping the mandible in a forward position.
4. The glossopalatinus muscle which elevates the back of the tongue into the palate.
5. The orbicularis oris muscle controls lip closure necessary for nasal breathing.

These eight muscles (3 are in pairs) which account for actually eleven muscles that surround the oral cavity and are all in contact with the margins of all of the various appliances (C, IG, G, N) when vibration is instituted.

The vibrating device contacts and vibrates all of these muscles via the outer margins of the appliances that can increase the blood flow and oxygen to these muscles. These muscles are those that influence in keeping the mandible in a closed position (masseter), in a forward position (internal and external pterygoids), keeps the tongue in a forward position (genioglossus), keeps the tongue elevated (glossopalatinus), and keeps the lips closed and to lengthen the lips (orbicularis oris). This also has the ability to strengthen the lips to aid in keeping the appliance in the mouth. These are the same muscles that are used in various exercises recommended when using the Habit Corrector as well as in the use of the C, IG, G, and N as well as by myofunctional therapists.

The vibrations can increase the blood circulation and blood oxygen level and as a result increase the strength and durability of these muscles that are in contact the various appliances as well as increasing growth of both the mandible, maxilla and the muscles. The increased strength of the muscles as well as the increased endurance both are responses from the increase in oxygen level. This increases the efficiency of correcting various habits such as:

1. Mouth breathing during the day or night.
2. Increase nasal breathing.
3. Poor tongue posture position within the mandibular body instead of being properly elevated within the palate.
4. Open mouth resting posture.
5. Abnormal tongue thrust.
6. Abnormal swallowing called reverse swallowing which includes a tongue thrust.
7. Distal slipping of mandible during sleep.

Therefore, it would be a great help to correct various habits by increasing the strength and efficiency of the muscles and increasing their stability with an increase in blood circulation with vibration and with the increase in blood oxygen which increases growth of both bone and muscles.

In one embodiment, there is provided a method of increasing blood circulation to encourage tooth eruption in a dental patient. The method includes: providing a dental appliance to the dental patient; connecting a pulsation device to the dental appliance to cause the dental appliance to vibrate; inserting the dental appliance into the patient's oral cavity; transmitting vibrations to various muscles of the oral cavity though the inserted dental appliance to encourage tooth eruption in the dental patient.

In another embodiment, there is provided a method of correcting overbite of a patient. The method includes: providing a dental appliance having eruption guidance features; connecting a pulsation device to the dental appliance to cause the dental appliance to vibrate; inserting the dental appliance into the patient's oral cavity; and transmitting vibrations to the patient's dentition through the inserted dental appliance to enhance eruption of the posterior teeth in order to stabilize the resulting eruption.

In a further embodiment, there is provided a method of increasing the speed at which deciduous teeth erupt. The method includes: providing a dental appliance having eruption guidance features; connecting a pulsation device to the dental appliance to cause the dental appliance to vibrate; inserting the dental appliance into the patient's oral cavity; transmitting vibrations to the patient's dentition from the vibrating dental appliance; and applying a biting pressure to the appliance and releasing the biting pressure from the appliance for a predetermined period of time to increase the force and speed of tooth eruption.

BRIEF DESCRIPTION OF THE DRAWINGS

The above-mentioned aspects of the present application and the manner of obtaining them will become more apparent and the teachings of the present application itself will be better understood by reference to the following description of the embodiments of the present application taken in conjunction with the accompanying drawings, wherein.

Corresponding reference characters indicate corresponding parts throughout the several views. Although the exemplification set out herein illustrates embodiments of the present application, in several forms, the embodiments disclosed below are not intended to be exhaustive or to be construed as limiting the scope of the present application to the precise forms disclosed.

DETAILED DESCRIPTION

While exemplary embodiments incorporating the principles of the present disclosure have been disclosed herein, the present disclosure is not limited to the disclosed embodiments. Instead, this application is intended to cover any variations, uses, or adaptations of the disclosure using its general principles. Further, this application is intended to cover such departures from the present disclosure as come within known or customary practice in the art to which this invention pertains.

The present disclosure is directed to the use of a pulsation device to apply a pulsation force directly to a preformed eruption guidance appliance. The preformed eruption guidance appliance is placed in an individual's mouth to fit the appliance to the individual's teeth. Once properly located, the pulsation force is applied to the teeth through the appliance which increases the force and speed of eruption, in a natural way, to increase the space available for more severely predicted crowding of dentitions. This technique, i.e. process, also increases the efficiency of forceful eruption of an erupting tooth to more effectively and efficiently position the tooth or teeth into the preformed tooth socket or sockets of the appliance.

The eruption guidance appliances are not custom made to fit an individual since the erupting teeth are often still buried below the gum tissue. In addition, other eruption guidance appliances, which are also not custom made, are used for erupting teeth that have erupted through the gum tissue. Such eruption guidance appliances are made in different sizes to accommodate individuals of different sizes. As a result, the socket anatomy and size of the appliance selected for an individual are based on an appropriate predicted size using various measuring techniques. Using the results of the measuring techniques, one of a variety of different appliances is selected for the individual. As the tooth erupts outside of the tissue, it is gradually directed into its appropriate preformed socket. With the applied pulsation, transmitted from the pulsation device to the appliance, through the appliance, and to the teeth, the erupting teeth are more efficiently and effectively guided into their predicted sockets as a result of the increased speed and force of eruption. The pulsating device by transmitting vibrations via the appliance to various muscles of the oral cavity that can increase the efficiency and strength of the muscles to aid in closure of the lips, increasing the width of the palate, prevents the mandible from slipping posteriorly during sleep that can reduce the opening of the oropharynx, and aid in keeping the tongue elevated in the palate which prevents mouth breathing all by increasing the blood and oxygen supply to these various muscles.

Figure 1:
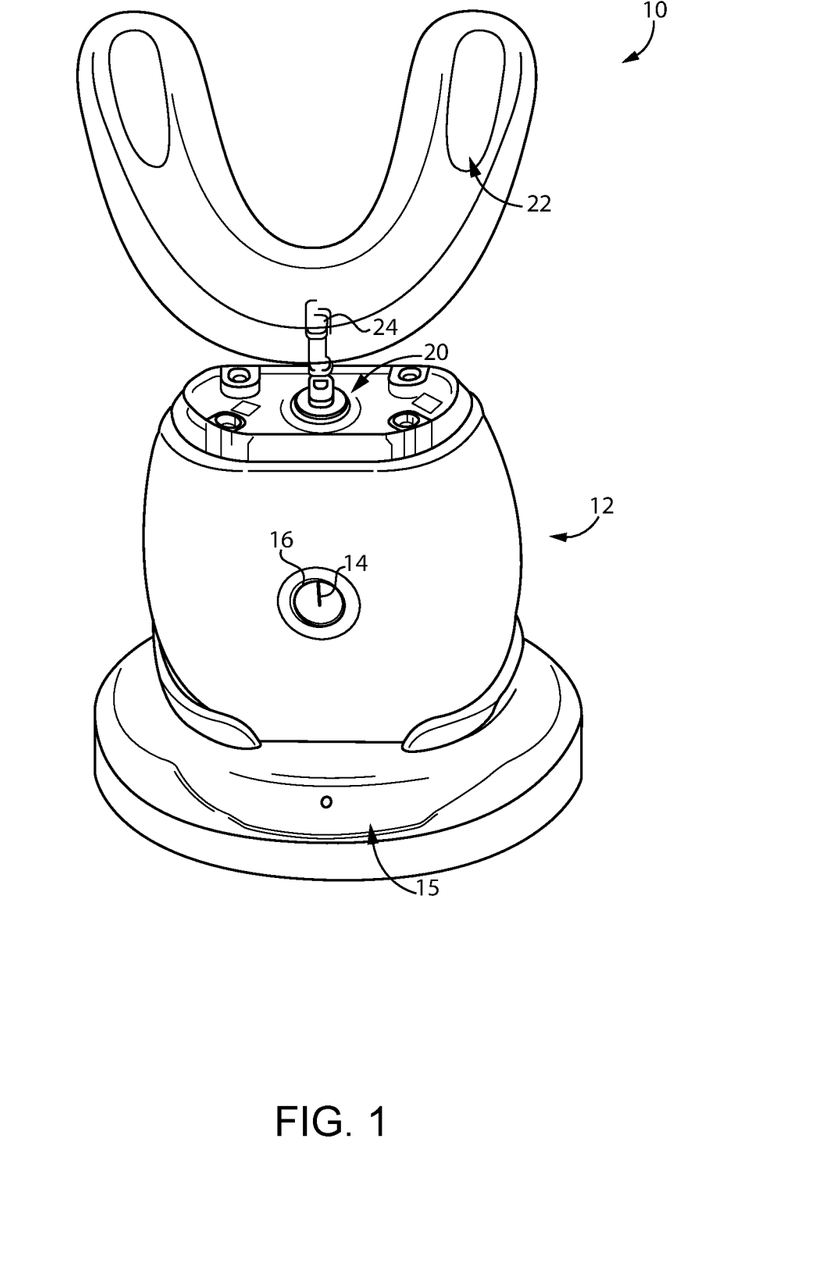
FIG. 1 is a front elevational view of a device to encourage tooth eruption.

FIG. 1 illustrates a device 10 to encourage tooth eruption toward a preferred location and a preferred alignment as well as providing increased blood flow and blood oxygen flow to an individual. The device 10 includes a hand-held pulsation device 12 that includes a power button 14 that enables a user to turn on and to turn off the pulsation device 12. The pulsation device 12, in one embodiment, includes one or more rechargeable batteries that are recharged by a charging station 15. The charging station 15 includes a charging cord (not shown) that is configured to receive a USB cable for charging the pulsation device 12, as is understood by those skilled in the art. In other embodiments, the pulsation device 12 does not include one or more rechargeable batteries, but instead includes disposable batteries. When the pulsation device 12 is seated on the charging station 15, the rechargeable batteries are charged if needed. While the rechargeable batteries are being charged, a charging indicator 16, such as a light, indicates that the one or more batteries are being charged.

The device 10 further includes an appliance connector 20 that extends from the pulsation device 12 and which is coupled to a preformed eruption guidance appliance 22. As described herein, the preformed guidance appliance 22 is selected from a range of guidance appliances, each of which is selected by size and shape to fit an individual based on the individual's anticipated growth profile. In some embodiments, a single preformed guidance appliance is sufficient to provide the desired growth pattern of the teeth and jaws. In other embodiments, more than one preformed guidance application is needed to provide the desired growth pattern.

The pulsation device 12 is configured to continuously move the connector 20 upon activation of the power button 14. The continuous movement of the connector 20, in different embodiments, moves rapidly in one or more directions with respect to the pulsation device 12, for instance in any one of or in between any one of X, Y, or Z directions, where the Y direction extends longitudinally with respected to the device 12 and along the connector 20, the X direction being substantially perpendicular to the Y direction and along a plane defined by a bottom surface of the appliance 22, and the Z direction being perpendicular to both the X and Y directions.

The pulsation device 12 is configured to apply pulsation signals to the connector 20 which in turn vibrates the preformed guidance appliance 22 in the directions applied by the moving connector 20. In one embodiment, the connector 20 is held in place at the pulsation device 12 and includes a male end 24 that fits within and is held by a female connector located in the appliance 22. In other embodiments, each of the preformed guidance appliances 22 includes a connector 20 fixedly held by the appliance 22. In these embodiments, the connector includes a free male end that is inserted into a female connector located in the pulsation device.

Figure 2:
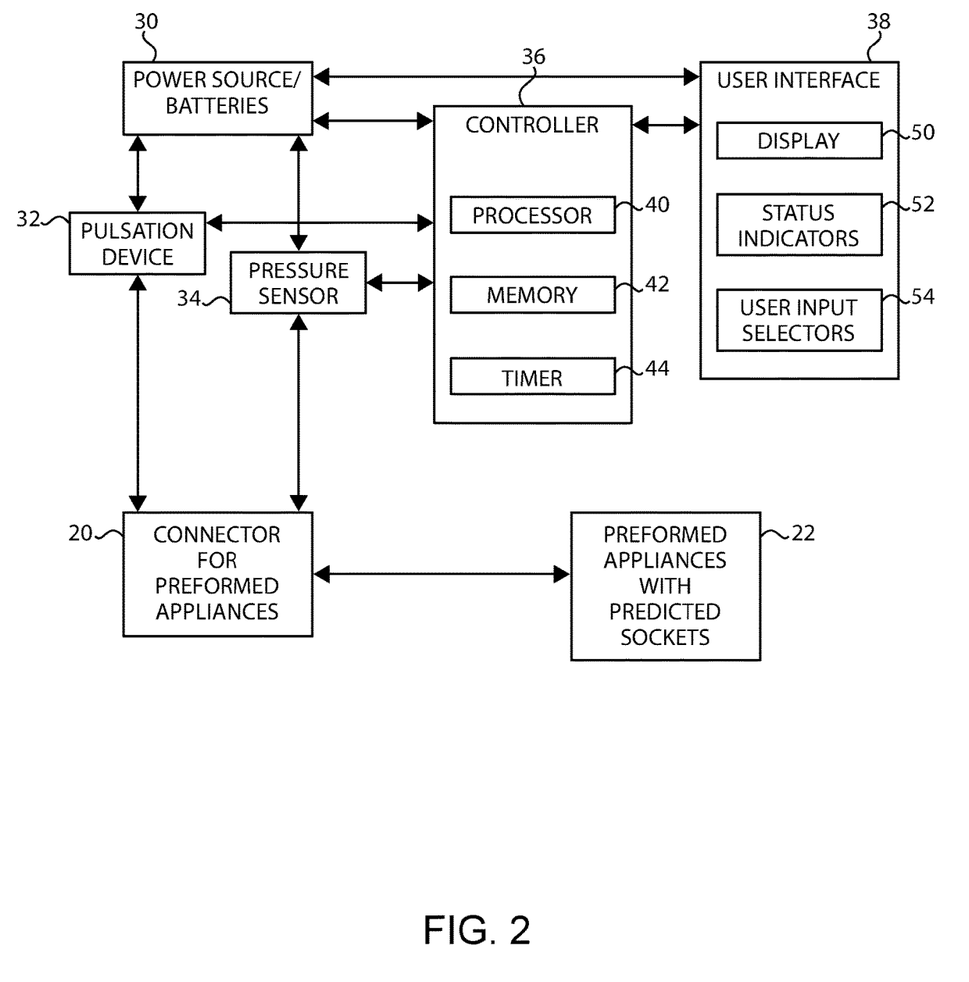
FIG. 2 is a block diagram of a device to encourage tooth eruption.

FIG. 2 illustrates a block diagram of the tooth eruption guidance device 10 including a power source 30 which includes rechargeable batteries or disposable batteries. The power source 30 provides a source of power for a pulsation device 32, a pressure sensor 34, a controller 36, and a user interface 38. The controller 36 is configured to control the operation of the device 10 including controlling the operation of the pulsation device 32 and determining a pressure applied to the preformed appliance 22 with a pressure sensor 34. In one embodiment, the pressure sensor 34 is a piezoelectric pressure transducer that determines if a pressure is being applied by the user to the guidance appliance 22. By sensing pressure applied, an additional level of confirming use of the device during a guidance session is provided. The controller 36 is further coupled to a user interface 38 which receives inputs provided by a user or which indicates a number of different operational states of the device.

The controller 36, in different embodiments, includes a computing device or other programmable devices, which are either firmware controlled devices or software controlled devices, or a combination of both firmware and software controlled. In these and other embodiments, the controller 36 includes one or more of the processors 40 (e.g. microprocessors). An associated memory 42 can be internal to the processor or external to the processor(s). The memory 42 includes, in different embodiments, random access memory (RAM) devices comprising the memory storage of the controller 36, as well as any other types of memory, e.g., cache memories, non-volatile or backup memories, programmable memories, or flash memories, and read-only memories. In addition, the memory 42 can include any cache memory in a processing device, as well as any storage capacity used as a virtual memory, e.g., as stored on a mass storage device or another computer coupled to controller 36. A timer 44, which is either internal to the controller 36, as illustrated, or external to the control 36, provides a timing function to enable a user to time the use of the device 10. Upon pressing a start button, the device 12 starts applying a pulsation signal to the guidance appliance 22. In one embodiment, the power button 14 operates as a start button by an initial depression of the button 12 or by a selected number of button pushes. For instance, in some embodiments, a single actuation of the power button 14 turns on the device and a second actuation of the power button 14 starts the pulsation.

Memory storage, in other embodiments, is located in a cloud system, also known as the "cloud", where the memory is located in the "cloud" at a distant location from the device 10 to provide a storage location for device operating information, such as device usage. For instance, in one embodiment, the processor 40 keep causes usage information to be stored in the memory 42, which can be downloaded to the cloud storage through the internet. Such information can include usage patterns including the day, the time of day, and the duration of use during the day. When referring to the controller 36, the processor 40, and the memory 42, other types of controllers, processors, and memory are contemplated.

The controller 36 executes or otherwise relies upon computer software applications, components, programs, objects, modules, or data structures, etc. Software routines resident in the included memory 42 of the controller 36, or other memory, are executed in response to the signals received from the power source 30, the pulsation device 32, the pressure sensor 34 and the user interface 38, each of which provides a signal to the controller 36.

The user interface 38 includes a display 50, one or more status indicators 52, and user inputs 54. The display 50 in different embodiments includes an LED screen or individual illumination devices. For instance, the LED screen can be configured to display the on/off status of the device, the amount of time selected to apply the pulsation signals to the appliance 22, or the amount of time remaining during a pulsation session. In other embodiments, the display 50 is a row of illumination devices, i.e. lights, that indicated durations of time selected deepening on the number of lights illuminated at the same time. In other embodiments, all lights in the row of lights are illuminated at the start of a guidance session, and a time passes each one of the lights is turned off as periods of time elapses. One or more status indicators 52 are included and provide one or more statuses of the device, for instance the device being on or off or the amount of power remaining in the batteries.

Figure 3A:
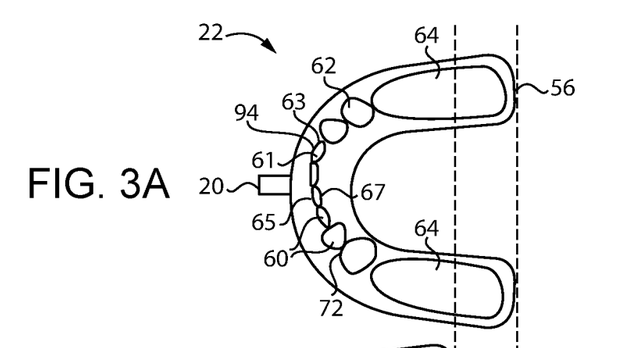
FIG. 3A is a top perspective view of a corrective dental appliance, for use with a pulsation device, having slots for multiple teeth after the first permanent molars have erupted in a six to eleven year old.
Figures 3B, 3C:
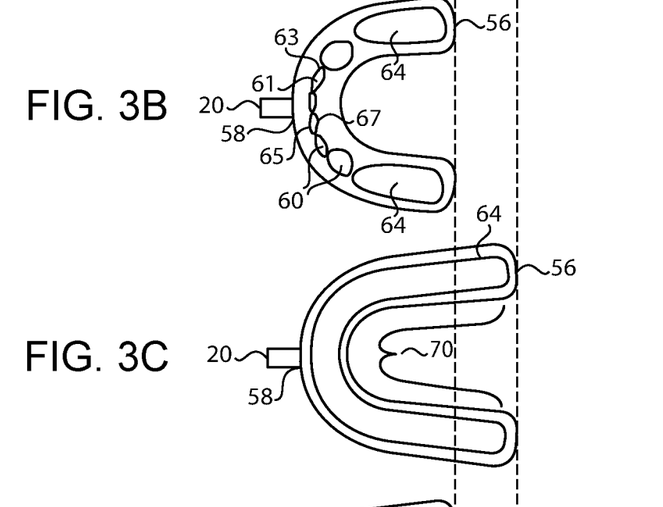
FIG. 3B is a top plan view of another embodiment of a corrective dental appliance, for use with a pulsation device, having slots for multiple teeth before the first permanent molars have erupted in a youth under the age of six.
FIG. 3C is a top plan view of a dental appliance, for use with a pulsation device, having one slot for multiple teeth after the first permanent molars have erupted in a six to eleven year old.

The preformed eruption guidance appliances 22 include, but are not limited to, the eruption guidance appliances as illustrated in FIGS. 3A to 3E. Referring now to FIG. 3A, the dental appliance includes a first end 56 and a second end 58. Teeth sockets 60 may either be a single tooth slot 62 or a multiple tooth slot 64. The single tooth slot 62 may fit one tooth of the patient and the multiple tooth slot 64 may fit more than one tooth of the patient. The multiple tooth slot 64 may fit, for example, the second bicuspid and first permanent molar of a patient. More specifically, the multiple tooth slot 64 may fit the first and second deciduous molars and first permanent molar of the patient, for example, between the ages of eight and eleven. The multiple tooth slot 64 may be designed, for example, for the patient who does not have the adult second molars present distal to the V-V line, as seen in FIG. 3C. Further, the multiple tooth slot 64 may accommodate all of the teeth of the patient with no individual teeth sockets 60. Additionally, protruding ribs (not shown) on the mesial side 61 and/or distal side 63 of the teeth and/or on a labial surface 65, or a lingual side 67 of the teeth.

Figure 3D:
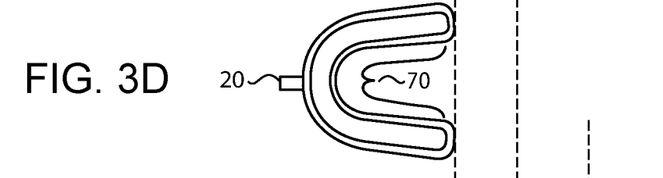
FIG. 3D is a top plan view of a dental appliance, for use with a pulsation device, having one slot for multiple teeth before the first permanent molars have erupted in a youth under the age of six.
Figure 3E:
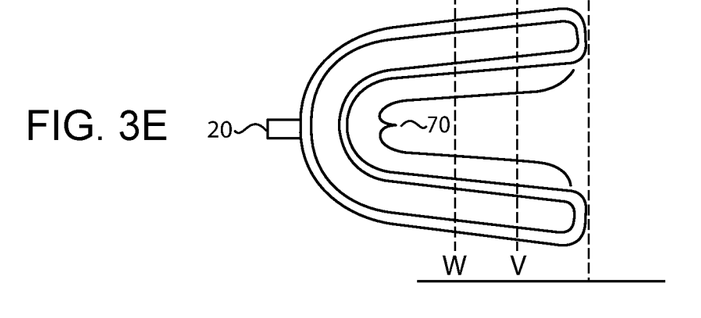
FIG. 3E is a top plan view of a dental appliance, for use with a pulsation device, having a multiple tooth slot after the first and second permanent molars have erupted in an individual twelve years or older.

Referring now to FIG. 3B, the multiple tooth slot 64 may be designed, for example, to fit the first and second deciduous molars of the patient. More specifically, the multiple tooth slot 64 may be designed, for example, for a patient under the age of six years of age. However, the multiple tooth slot 64 may not have any slot for the first permanent molar distal to the W-W line. Additionally, the multiple tooth slot 64 may fit all of the teeth of the patient after the first permanent molars have erupted distally to the W-W line for children aged six to eleven, as illustrated in FIG. 3C. Additionally, the multiple tooth slot 64 may be designed where no permanent molars are present distally to the W-W line for patients under six years of age, as illustrated in FIG. 3D. Further, the multiple tooth slot 64 may fit the first permanent molars positioned distally to the W-W line and/or including the second permanent molars distal to the V-V line, as illustrated in FIG. 3E.

When a patient is expected to lose deciduous teeth and/or have permanent teeth replace the deciduous teeth, the teeth sockets 60 may be predicted based on the sizes and shapes of the already-erupted permanent teeth of the patient and/or from group standards. In addition, if the patient has some permanent teeth which are unerupted or erupting at the time, the teeth sockets 60 may be predicted based on the sizes of already-erupted permanent teeth of the patient.

The entire dental appliance 22 may have teeth sockets 60 if all of or almost all of the permanent teeth have yet to erupt. The unerupted tooth or teeth or partially-erupted permanent tooth crown may be predicted from a digital or standard x-ray image. The entire dental appliance 22 may be based on predicted tooth sizes and shapes as well as the shape and size of the upper and lower arches of the patient and/or from group standards.

Figure 4:
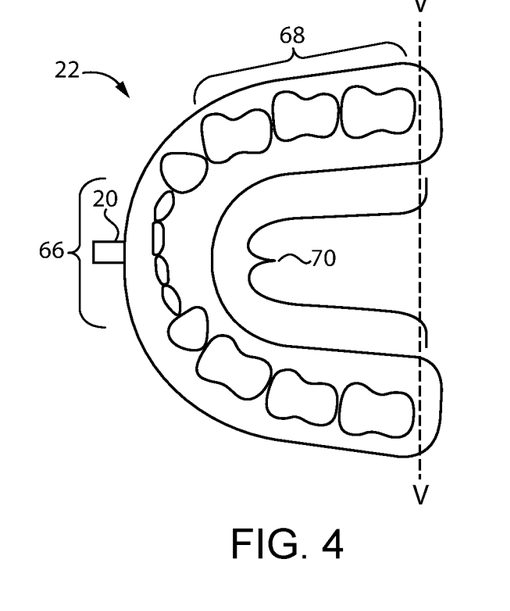
FIG. 4 illustrates a top plan view of an appliance for use with a pulsation device.

The dental appliance 22 may be created manually or by the computer. Additionally, the dental appliance 22 may have some areas formed by the computer as a replication of a portion of the dentition of the patient for retainability. The portion of the dentition of the patient used for retainability may remain stable during the period of incisal eruption. A youth aged five to seven, for instance, may be expected to have any number of the upper and/or lower permanent incisors erupted or in the process of eruption. In such a case, the dental appliance 22 may have one or more predicted tooth areas 66. See FIG. 4. If all of the adult teeth of the patient are not yet located in the mouth of the patient, certain areas may need to be predicted from the size and shape of the existing permanent teeth. Therefore, measurements of the first permanent molars and/or adult incisors may be necessary if present in the mouth. If no adult teeth are present in the mouth, the size of one or more incisors may be estimated from a digital or standard x-ray view by an intra-oral or panoramic radiograph. The computer-generated dental appliance 22 or manually created dental appliance 22 may be partly a replica of the cast of the patient and/or partly a prediction of the size and shape of the teeth expected to erupt into the mouth. In addition, the computer-generated dental appliance 22 or the manually created dental appliance 22 may have the duplicated tooth area 68 of FIG. 4 and/or the predicted tooth area 66 made into cast(s) from which the dental appliance 22 or graduated dental appliances may be made. In either case, certain areas of groups of teeth may be combined into a single tooth slot 62 or a multiple tooth slot 64 of FIG. 3A. Further, the dental appliance 22 may have one or more single tooth slots 62 and/or multiple tooth slots 64. The multiple tooth slot 64 may allow for certain areas, for example, the upper and/or lower posterior teeth to expand and also to adjust forward through the leeway space. These devices and others described herein are considered as eruption guidance devices. In one or more eruption guidance devices, the overbite is corrected by increasing the vertical dimension of the shields toward and past the gumline and pulsation techniques enhance the eruption of the posterior teeth in order to stabilize the result.

In the computer-generated dental appliance 22 intended for an individual aged four to seven, a determination may be made if crowding of the permanent teeth is anticipated following eruption or if sufficient room is present in the arch 70. Additionally, a determination may need to be made if an interproximal space 72 will eventually be present. The computer can accomplish such an arch length analysis based on a difference between the measurement of the widths of permanent teeth expected to erupt into the mouth and the amount of space available for the eruption of the teeth. An amount of anticipated increase in arch 70 due to normal eruption may also be factored into the analysis.

If crowding is anticipated, the computer-generated model, dental appliance 22, or appliances, may be enlarged approximately 3.0 mm. from lower deciduous canine-to-canine dimension while the lower adult centrals may be erupting. In addition, the computer-generated model, dental appliance 22, or appliances, may be enlarged another 1.0 mm. while the lower adult laterals may be erupting. Further, similar arch 70 expansions may be incorporated into the posterior segments. For example, the arch 70 expansions may be slightly smaller. The dental appliance 22 may not be intended to expand the arch 70, but the dental appliance 22 must be large enough to allow for natural expansion as the incisors force their way into the arch 70. The expansion of the incisors may be accomplished as the incisors force their way into either the single tooth slot 62 or the multiple tooth slot 64.

If a close fit of the dental appliance 22 is desired and only deciduous teeth are in place, the computer-generated dental appliance 22 may duplicate only those teeth that will be in the mouth for at least enough time until another dental appliance 22 may be used or until the front adult incisors have fully erupted. If some deciduous teeth are expected to exfoliate within a short period, the predicted tooth area 66 and teeth sockets 60 may be formed by the computer. The teeth sockets 60 may be sized and/or shaped for the incoming permanent teeth, which may replace the exfoliated deciduous teeth after the first permanent molars erupt. Adjustments may need to be made to the dental appliance 22 to allow for the mesial drift that closes the leeway space. The leeway space may be the space created by the size difference between the wider deciduous posterior teeth and the narrower permanent teeth which replace them. To solve this, a dentist or orthodontist may provide a larger size of the dental appliance 22 to the patient which may allow expansion for arch 70 to take place. In addition, the dentist or orthodontist may provide the dental appliance 22 with the multiple tooth slot 64 instead of the single tooth slot 62.

Figure 5:
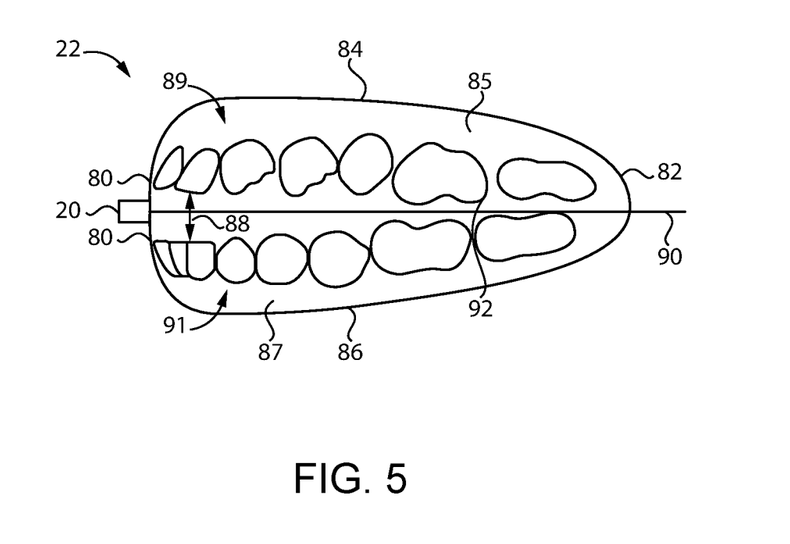
FIG. 5 illustrates a side view of a dental appliance for use with a pulsation device.

Referring now to FIG. 5, the dental appliance 22 may have a front end (mesial) 80, a back end 82 (distal), a top end 84 of a top portion 85, or top half, and a bottom end 86 of a bottom portion 87, or bottom half. In one embodiment, the top portion 85 and the bottom portion 87 are pivotally connected by a living hinge at the back end. Additionally, the dental appliance 22 may have material between the upper and lower teeth or within the freeway space 88. The amount of material at the front end 80 of the dental appliance 22 may be greater than the amount of material at the back end 82 of the dental appliance 22. In addition, the altered freeway space 88 may improve overbite corrections when the amount of the material is increased in the front end 80 of the dental appliance 22 and decreased in the back end 82 of the dental appliance 22. In one embodiment, the connector 20 of FIG. 1 is inserted into a hole located in the front of the appliance. The connector 20, which in one embodiment is a rod, is attached to the appliance 22 by forcing the rod into the hole which is then held in place by a friction fit. In this way, additional appliances of other types, sizes, and configurations are compatible with the vibrating device.

The top portion 85 includes an upwardly extending outer shield 89 and the bottom portion 87 includes a downwardly extending outer shield 91. Upper and lower inner shields, not shown, are spaced from their respective outer shields 89 and 91. Each of the shield have upper terminating edges that extend past the gumline of a patient to contact the gums at both the upper and lower jaws. In this way, the gums receive pulsation from the vibrating device which increases force and speed of tooth eruption and improve the dental intercuspation and speeds its correction.

Further, the altered freeway space 88 may aid in open-bite corrections if the alterations are reversed, wherein less of the material may be implemented in the front end 80 and more material may be implemented in back end 82. Still further, if the front end 80 of the dental appliance 22 is increased at the freeway space 88 and reduced in the back end 82, an overbite may be corrected. Additionally, if the freeway space 88 at the front end 80 is reduced and the freeway space 88 at the back end 82 is increased, an openbite may be corrected. Additionally, a slit (not shown) may be created vertically between the upper and lower incisal edges in the front end 80 which may correct, for example, openbite.

To allow for eruption, especially of the posteriors during growth, less vertical inter-occlusal material 90 may need to be incorporated into the computer program. In addition, extra space may be provided in the occlusal surface 92 while maintaining the fit around the gingival undercuts. The extra space may be needed, for example, to allow the teeth to be able to erupt properly. Further, the extra space may be needed, for example, to allow the teeth to erupt more completely during growth. At the same time, more material may be present in the anterior segment of the freeway space 90 which may aid in the correction of overbite by restricting the vertical eruption of the incisors. In addition, alterations, such as a flattening of the occlusal surface 90 and/or the multiple tooth slot 64 of the posterior teeth may allow any tooth, regardless of the occlusal anatomy of the tooth to properly fit or erupt into the single tooth slot 62 or the multiple tooth slot 64 of the dental appliance 22. Additionally, incisal edges 94 (see FIG. 3A) may be thinned to allow the teeth to erupt into the dental appliance 22 properly without rotations.

Furthermore, a similar situation may occur when the remaining adult teeth erupt when the patient is around ten years of age. It should be understood that the multiple tooth slot 64 may be provided instead of the single tooth slot 62. Further, the multiple tooth slot 64 may cover the entire dental appliance 1 and may be provided in one or several sizes. Please also see U.S. Pat. No. 8,133,050 having the title "Dental Appliance Having a Duplicate Tooth Area and/or Predicted Tooth Area and a Method for Correcting the Position of the Teeth of a Patient", which is incorporated by reference herein in its entirety.

In addition to the preformed appliance described herein and in U.S. Pat. No. 8,133,050, the pulsation device 12 of FIG. 1, in other embodiments, is used with a preformed appliance described in U.S. Pat. No. 6,626,664, which is incorporated by reference herein in its entirety. In this type of preformed appliance, increasing tooth eruption not only applies to the anterior teeth at a younger age but also for the premolars and permanent molars at older ages even up into the adult. For example, an appliance as described in U.S. Pat. No. 6,626,664 is used specifically during fixed orthodontic treatment. The appliance is worn over the dentition that has brackets or bands cemented or bonded to the individual teeth and arch wires. The purpose of this appliance is to advance the mandible to aide in the esthetics of the soft tissue facial profile (correction of the overjet) and to correct an excessive overbite by encouraging the over eruption of the $1^{st}$ and $2^{nd}$ permanent molars. In this way the lower face height is increased and the vibration of the dentition and surrounding tissues, occurring in response to the pulsation device applied to the appliance, increases the strength, speed and efficiency of eruption. See also Applicant's patent application entitled Wire and Ramps in Sleep Habit Corrector, filed Jun. 29, 2021, having the Ser. No. 17/361,713, describing an appliance, that in one embodiment, is used with the pulsation device 12 and an appropriate connector 20, and which is incorporated by reference herein in its entirety.

In a similar way the correction of overbite by eruption guidance appliances preformed orthodontic appliances open up the lower face by having more material by the front teeth than the back teeth. See for instance U.S. Pat. Nos. 5,876,199; 7,234,933; 7,458,810; 7,963,765; 8,870,566, each of which is incorporated by reference herein. This opens up the overbite and then the back teeth must erupt to stabilize the result which can take advantage of pulsation of speed and more complete ideal (without rotations) eruption of these posterior teeth. In some embodiments and for some users, the device 10 increases the development of collagenous fibers. This same technique can use increased eruption when using the appliance disclosed in U.S. Pat. No. 7,234,933 in the permanent dentition since it also depends on the eruption of the posterior teeth to correct and stabilize the correction of the overbite and overjet. See for instance, U.S. Pat. Nos. 3,898,736 and 7,458,810, each of which are incorporated by reference herein.

In another example of increasing the efficiency of tooth eruption using the disclosed device 10, correction of TMJ (temporal mandibular joint) problems is provided. Preformed appliances such as those disclosed herein are attachable with the appropriate connector 20. By using the pulsation device 12, with such preformed appliances designed to correct TMJ problems, the user can experience a more rapid correction of TMJ problems. See for instance, U.S. Pat. No. 7,458,810 as one example of a preformed appliance suitable for use with the pulsation device 12.

These TMJ preformed appliances, when connected to the described pulsation device 12, open up and advance the mandible. The eruption of the posterior teeth permanently opens and positions the mandible in an anterior position that moves the condyle forward in order to recapture (or reduce)

the anteriorly displaced disc. The success of the procedure depends on the obtaining sufficient eruption of the posterior dentition into a new increased vertical position. This is particularly important in the adult when all facial and jaw growth has terminated. Often the posterior teeth in such patients do not or are extremely slow in eruption. By including pulsation in such cases without waiting for several years for their eruption or even non eruption after these teeth are finished with erupting, can produce faster and more successful results.

Another example with the benefits of added eruption is during mandibular growth. As the mandible grows downward and forward, the upper and lower dentition must erupt to stabilize this growth. This eruption ensures normal face height to achieve an acceptable dimension for ideal facial esthetics. This application of the pulsation device to the appliance enhances acceptable mandibular growth and helps to maintain ideal downward and forward progress of the mandibular as well the maxilla, and also encourage sufficient tooth eruption. Additional oxygen provided by the pulsation device can increase the condyle, of the mandible and also increase maxillary growth.

In one embodiment, enhanced tooth eruption is provided when a user bites down forcibly for about five (5) minute and then releases the pressure for about 1 minute, while still holding the appliance 22 in the user's mouth. The application of force for 5 minutes followed by the release of pressure for one (1) minute is repeated for a total of two (2) hours per day. The total time-period of 2 hours per day is either continuous or is divided into separate time-periods per day, such as a first one hour session in the morning and a second one hour session in the afternoon or evening. In one or more embodiments, the amount of time of applying pressure using biting force is greater than the amount of time of pressure release. Other times of sessions are contemplated. The eruption of teeth in such user occurred earlier and with greater speed than an untreated user, such as a child. An increased level of eruption can be achieved by combining this biting and releasing with applied pulsation to the appliance 22 which enhances the force and speed of eruption than when either are used alone without the other. The pulsation provided by the pulsation device 32 occurs at the rate of 0.1-400 Hertz and with a force of 0.1 to 0.5 newtons, while the forces of biting down into the appliance can achieve up to 200-400 lbs. per sq. inch.

While the disclosed embodiments with the inclusion of vibration provide for enhanced tooth eruption, the embodiments additionally provide increased blood flow and blood oxygen flow to an individual. As described herein, the use of the present embodiments, by combining pulsation through speech and habit correction appliances (i.e. habit correctors) increases oxygen supply to the dentition and its supporting soft tissue and bone. This application of pulsation to the habit correctors has a direct effect on the speed of tooth eruption and to various muscles of the oral cavity. This is possible due to the contact of the appliance with the muscles surrounding the appliance, namely the masseters, tongue muscles, and the orbicularis oris around the lips. The use of the habit correctors is enhanced when the patient is using the pulsated appliance in the mouth while the patient squeezes all of the muscles against the outer margins of the appliance. The outer margins of the appliance include the inner surfaces and top edges of the outer shields 89 and 91 and the inner shields that are spaced from the respective outer shields. This ensures that the muscles are well vibrated at the same time as the teeth, and stimulates the blood flow and the oxygen to both muscles and dentition. Issued patents illustrating habit correctors include the following, each of which is incorporated herein by reference: U.S. Pat. Nos. 7,234, 933; and 7,458,810.

The use of the pulsated habit correctors can significantly aid in several areas in treatment of sleep problems and habits that often contribute to the presence of sleep issues in children. Speech problems are also addressed particularly by the device being in contact with the tongue and lips or vibration applied to the teeth which is transmitted to the tongue, lips, muscles, and other tissues. The strengthening of these muscles with increased oxygen can be valuable in overcoming several issues. Oral habits can be overcome that otherwise would have a direct effect on normal sleep. One oral habit is mouth breathing which is directly related to the strength and length of the lips in developing closed lips in sleeping. In one or more embodiments, treatment involves some daytime wear with the patient actively closing the lips over the front area of the habit corrector. Any increase in the strength of the muscles accentuated with the increase of blood flow, oxygen and possible hormones, improves an individual's sleep experience and improve sleep by preventing the mandible from drifting posteriorly (external and internal pterygoid muscles) and thereby keeping the oropharynx open that aids the endocrine systems and its growth hormones. This stimulation of growth can aid in the proper length of the lips.

Figure 6:
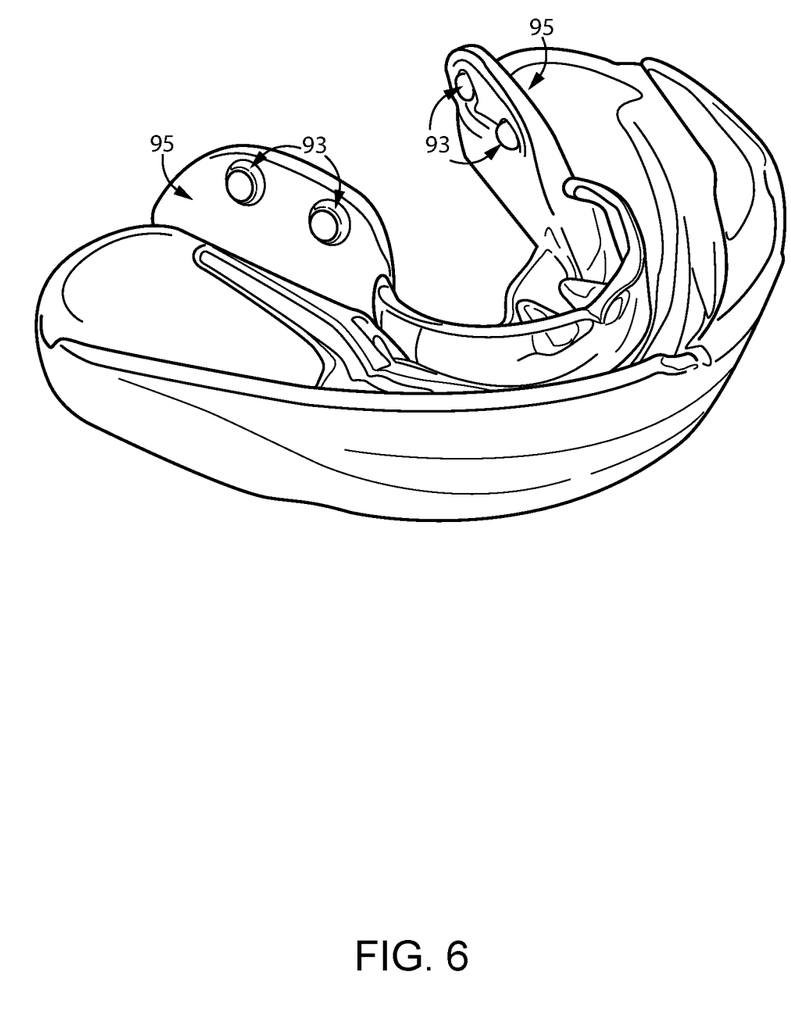
FIG. 6 illustrates a perspective view of a habit corrector appliance.

Strengthening of the tongue with increased blood flow and oxygen can help with both the widening of the upper posterior arch, since the tongue is forced to be elevated in its resting posture within the palate (glossopalatinus muscles). A habit corrector appliance, as seen in FIG. 6, includes palatal buttons 93. The palatal buttons 93 extend from an inner shield 95 and encourage the patient (when instructed as to use) to use the tongue to apply lateral pressure to the inner shield 95 at the buttons 93 which increases the palatal width and increases normal nasal breathing. This strengthening of the tongue by use of the pulsating device aids in this widening as a result in the increased blood flow and oxygen level in the tongue muscles that in turn aids in normal nasal breathing as well as preventing mouth breathing. While two palatal buttons 93 are shown extending from each side of the shield 95, other numbers of palatal buttons 93 are contemplated. In addition, while the palatal buttons 93 are shown as being round, other shapes and sizes of palatal buttons are contemplated.

Mouth breathing at night is the major factor in its adverse effect on neurocognitive and behavior symptoms as a result of the constriction of the oropharynx. This lack of incoming air into the lungs has a direct effect of the brain, immune and endocrine systems in the body. When the tongue positions itself in the palate instead of an established habit of positioning it within the mandibular body, mouth breathing becomes impossible and as a result increases normal nasal breathing. This elevated tongue position also prevents the tendency for nighttime mouth breathing. Nighttime breathing allows the base of the tongue to be displaced resulting in contact against the anterior wall of the oropharynx which exerts pressure on the airway which can close the airway either partially or entirely. The increased muscle activity of the genioglossus muscle prevents the base of the tongue from impinging on the anterior wall of the oropharynx.

These and other problems involving undesirable sleep habits, in particular, are overcome. By establishing normal nasal breathing with the elimination of mouth breathing, normal lip closure at rest while breathing is developed during the day and night but especially at night, and is beneficial in providing normal nasal breathing. When a person sleeps, if the lips stay closed and the mandible, for the most part, resists slipping distally as the muscles relax, the following muscles are directly impacted: 1) Masseter muscle which functions for jaw closure and resists its opening; 2) Internal pterygoid which is attached to the tuberosity and neck of the mandible aids in keeping the mandible from slipping distally; 3) external pterygoid muscle which also aids in keeping the mandible in a forward position; 4) the glossopalatinus muscle which elevates the back of the tongue into the palate, and 5) the orbicularis oris muscle controls lip closure necessary for nasal breathing and 6) the genioclossus muscle keeps the tongue from displacing posteriorly during sleep.

These nine muscles (3 are in pairs), which account for actually nine muscles that surround the oral cavity, are all in contact with the margins of the habit corrector when vibration is instituted.

The pulsation device 12 contacts and vibrates all of these muscles via the outer margins of the appliances which can increase the blood flow and oxygen to these muscles. These muscles are those that influence in keeping the mandible in a closed position (masseter), in a forward position (internal and external pterygoids), keeps the tongue in a forward position (genioglossus), keeps the tongue elevated (glossopalatinus), and keeps the lips closed and to lengthen the lips (orbicularis oris). These are the same muscles that are used in various exercises recommended when using certain types of habit correctors as well-being exercised based on exercises recommended by myofunctional therapists.

The vibrations resulting from the application of the pulsation device to the appliance can increase the blood circulation and blood oxygen level and, as a result, increase the strength and durability of these muscles that are in contact with the various appliances as well as increasing growth of both the mandible, maxilla and the muscles. The increased strength of the muscles as well as the increased endurance are both responses from the increase in oxygen level. This increases the efficiency of correcting various habits such as: 1) mouth breathing during the day or night; 2) poor tongue posture position within the mandibular body instead of being properly elevated within the palate; 3) open mouth resting posture; abnormal tongue thrust; abnormal swallowing called reverse swallowing which includes a tongue thrust; and 4) distal slipping of the mandible during sleep.

The use of the device 10 provides, but is not limited to providing, the following advantages: 1) increasing the efficiency of training muscles to correct mouth breathing; 2) increasing the efficiency of training muscles to train the tongue to be positioned within the palate during resting posture: 3) increasing the efficiency of training muscles for normal swallowing which occurs 2× a minute during the day and 1× a minute during the night; 4) increasing the efficiency of training muscles to prevent the mouth from opening; 5) increasing the efficiency of training muscles to keep the lips closed at all times; 6) increasing the efficiency of training muscles to increase the growth and apposition and resorption of the mandible; 7) increasing the efficiency of training muscles to prevent the mandible from slipping posteriorly during sleep. 8) preventing having myofunctional therapy from a therapist; 9) helping to prevent collapse of the oropharynx; 9) all appliances (C, IG, G, N) help to prevent oropharynx collapse. (C and IG are preventive appliances to prevent the development of orthodontic problems, G and N are interceptive appliances that alter orthodontic issues; 10) can increase palatal expansion by widening tongue exercises against the palatal tabs present in the various appliances; 11) can increase the advancement of the maxilla in the Max A and Class III appliances; 12) can increase closure of the lips to prevent mouth breathing; 13) can increase the length of the lips; 14) can increase correction of mouth breathing; 15) can increase correction of abnormal swallowing; 16) can improve anterior positioning of tongue when asleep; 17) can replace certain types of myofunctional therapy; and 18) can obtain results in less time.

As described herein, the use of pulsation increases the force and speed of tooth eruption when used with the appliances to guide erupting teeth into predicted sockets, to enlarge the arch, to make room for larger permanent anterior teeth, or to correct rotations which stabilize the corrected teeth for future growth by developing fibers around straight teeth instead of crooked teeth.

The described appliances that provide eruption guidance correct the overbite by increasing the vertical dimension of the anterior freeway space of the appliance which in combination with the use of pulsation techniques enhances the eruption of the posterior teeth in order to stabilize the result.

The use of the pulsation devices increases the force and the speed of eruption in properly finishing correction of TMJ problems in combination with specifically designed appliances for TMJ abnormalities.

In different embodiments, pulsation techniques enhance the use of appliances that fit over fixed appliances to increase mandibular advancement and decrease severe overbites by increasing the force and speed of the eruption of the 1st and 2nd permanent molars that aid in overbite correction in fixed orthodontics.

The combination of applying pressure, i.e. active clenching and resting periods in combination with pulsations exceeds the efficiency of either one of these methods by increasing blood circulation.

Early eruption of the deciduous teeth can be speeded up with the use of biting and releasing forces on appliances for eruption guidance, such as the C, IG, G appliances, as well as the N series adult appliance in combination with pulsation techniques to increase the force and speed of tooth eruption and improve the dental intercuspation and speeds its correction.

The use of pulsation in appliances to increase midface deficiencies (Max A) and Class III issues (Class III appliance) can enhance the forward adjustment of the upper anterior dentition as well as the maxilla (Max A and Class III appliances) and aids in the distalization of the mandibular dentition (Class III appliances) as well as reduction in lower face prominence.

The introduction of pulsation in combination with a specially designed habit and abnormal sleep correction appliances benefit a patient's outcome significantly by reducing abnormal sleep issues.

The use of pulsation reduces the amount of exercising, clenching and release which requires considerable cooperation from a patient needed in the G and N appliances.

The vibration/pulsation applied to the appliance when used at very early ages, guides the eruption of the deciduous teeth in ages of from 6 months to 3 years of age.

The application of vibration/pulsation using the appliance provides additional expansion and cross bite correction.

Pulsation forces enhance arch expansion when used in combination with imbedded wires in the various appliances.

Additional advantages of the described devices and methods include one or more of the following:

1) The muscles surrounding the vibrating appliance have an increase in blood circulation;

2) The muscles surrounding the vibrating appliance increase their oxygen level;

3) The muscles surrounding the vibrating appliance have an increase in muscle strength and stamina for mandible, tongue and pharynx;

4) Various muscles touching the vibrating appliance are those that are used in the myofunctional aspects of the appliance use;

5) The masseter muscle with the increased blood circulation helps to keep the mouth from opening which causes mouth breathing and influences adversely many sleep symptoms as well as nasal breathing, mandible and tongue posterior positioning during sleep and pharyngeal muscles;

6) The internal pterygoid muscle with increase blood flow aids in the forward positioning of the mandible;

7) The external pterygoid muscle with increase blood flow aids in the forward positioning of the mandible;

8) The genioglossus muscle with increase blood flow helps to keep the tongue forward;

9) The glossopalatinus muscle with its increase blood flow helps to keep the tongue elevated in the palate;

10) The orbicularis oris muscle with its increased blood flow helps to strengthen and lengthen the lips to maintain their seal while breathing and to prevent mouth opening;

11) The vibration transmitted to the bone, especially the mandible, helps to stimulate growth as a result of increased oxygen;

12) The vibrating appliance speeds up the correction of habits such as mouth breathing, tongue thrust, abnormal swallowing and poor tongue positioning at rest, with a direct influence on abnormal sleep issues;

13) Increases tongue strength to widen the palate;

14) Speeds up tongue exercises to advance the maxilla and upper teeth with the Max A appliance;

15) Speeds up Class III correction in a similar way with the Class III appliance;

16) Speeds up Class III correction by distalizing the lower dentition as result of increased oxygen.

17) When the vibrating appliance is coupled with the clenching exercises with the G and N appliances, it speeds up tooth movement even more.

18) Vibration can aid in keeping the mandible in a forward position with pacifier use when mandibular growth is essential from birth up to 3 years of age; and, 19) Creates nighttime myofunctional therapy with wear of the appliance for automated exercises occurring with each smile.

As described herein, the applied vibration to increase tooth eruption also increases the force and speed of the eruption and therefore the efficiency of gaining more pressure of eruption. This benefit enhances the eruption of teeth, which causes the teeth to force themselves into the very thin incisal edges of the sockets. The described devices and methods therefore are more successful in the correction of problems of rotations and proper positions of the teeth into an ideal occlusion. Also, the described devices and methods aid in the better eruption of the 2nd and 3rd molars as well as the permanent bicuspids and canines. An increase in normal muscle efficiency substantially prevents abnormal function of the tongue and muscles of the lips which improves the proper function of the several mentioned muscles as a result of increased blood and oxygen which also improve jaw growth.

The pulsation by increasing the force of the muscles reduces the need for active wear involving muscle strength.

Due to individual sockets for the teeth while using pulsation provides more direct effect on each of the individual teeth with increased results. See FIGS. 3A and 3B illustrating appliances having individual tooth sockets. In addition, while the habit corrector appliance of FIG. 6 is illustrated having a tooth slot, in other embodiments, the habit corrector application of FIG. 6 is formed with individual tooth sockets such as those of FIGS. 3A and 3B.

In other embodiments, increasing the stiffness of an appliance with (a) less flexible molding material, (b) lining the appliance with a stiff plastic and (c) providing a direct duplication of the tooth anatomy in the appliance with direct contact of all teeth of the customized appliance all made of stiff plastic. Such an appliance (of any of the 3 above, a, b, c) increases the transmission of the pulsations directly to the dentition, muscles, bone and unerupted teeth as opposed to a softer more flexible plastic. As an illustrative example, in one or more embodiments, the appliance is made of a polymer having a durometer Shore A hardness of 75 or more. In other embodiments, the appliance is made of a polymer having a Shore A hardness of 75 or less but such appliances include liner of stiff plastic having a Shore A hardness of greater than 75. However, a person of skill in the art would recognize that other types of plastic materials can be utilized depending upon the hardness desired and the outcome to be achieved.

Although reference is made to appliances constructed or available in predetermined sizes, in still further embodiments, an appliance having increased stiffness is a custom-made appliance that includes individual teeth sockets which are custom fit to a patient. In this embodiment, the appliance includes teeth sockets that are configured for predicted tooth eruptions or which are configured for a patient's current teeth locations. In these embodiments, the harder material, i.e. plastic or other polymers, are in direct contact with the teeth and other tissues, including both hard and soft tissues.

Therefore, it is a great help to correct various habits by increasing the strength and efficiency of the muscles and increasing their stability with an increase in blood circulation with pulsation and with the increase in blood oxygen which increases growth of both bone and muscles. As described herein, the method and apparatus increase muscle strength around the oral cavity as well as to increase airflow into the lungs which delivers additional oxygen to the entire body for increasing the speed and force of tooth eruption. Tooth eruption is both directed to a preferred location and is stabilized.

While exemplary embodiments incorporating the principles of the present disclosure have been described herein, the present disclosure is not limited to such embodiments. Instead, this application is intended to cover any variations, uses, or adaptations of the disclosure using its general principles. Further, this application is intended to cover such departures from the present disclosure as come within known or customary practice in the art to which this disclosure pertains.

What is claimed is:

1. A method of increasing blood circulation to encourage tooth eruption in a dental patient comprising: providing a dental appliance to the dental patient; connecting a pulsation device to the dental appliance to cause the dental appliance to vibrate; inserting the dental appliance into the patient's oral cavity; transmitting vibrations to various muscles of the oral cavity through the inserted dental appliance to encourage tooth eruption in the dental patient and an increase of muscle strength; wherein the dental appliance comprises features configured to guide erupting teeth into predicted sockets; the predicted sockets are configured to make room for larger anterior teeth and to correct rotation of teeth; wherein the guided erupting teeth are stabilized by developing collagenous fiber as a result of the transmitted vibrations; applying a biting pressure to the appliance and releasing the biting pressure from the appliance for a predetermined period of time; wherein the predetermined period of time includes the application of biting pressure for a first predetermined period of time followed by the release of the biting pressure for a second predetermined period of time; and wherein the first predetermined period of time is substantially 5 minutes and the second predetermined period of time is substantially 1 minute.

2. A method of increasing blood circulation to encourage tooth eruption in a dental patient comprising: providing a dental appliance to the dental patient; connecting a pulsation device to the dental appliance to cause the dental appliance to vibrate; inserting the dental appliance into the patient's oral cavity; transmitting vibrations to various muscles of the oral cavity through the inserted dental appliance to encourage tooth eruption in the dental patient and an increase of muscle strength wherein the dental appliance comprises features configured to guide erupting teeth into predicted sockets; the predicted sockets are configured to make room for larger anterior teeth and to correct rotation of teeth; wherein the guided erupting teeth are stabilized by developing collagenous fiber as a result of the transmitted vibrations; applying a biting pressure to the appliance and releasing the biting pressure from the appliance for a predetermined period of time; wherein the predetermined period of time includes the application of biting pressure for a first predetermined period of time followed by the release of the biting pressure for a second predetermined period of time; and wherein the application of biting pressure and the release of biting pressure alternate repeatedly for total time-period of substantially 2 hours per day, wherein the total time period of substantially two hours per day includes a continuous session of 2 hours or includes two or more separate sessions per day having a total time-period of 2 hours.

3. A method of correcting overbite of a patient comprising:
providing a dental appliance having eruption guidance features, wherein the dental appliance having eruption guidance features includes a shield having a vertical dimension at the front of the shield extending past the patient's gum;
connecting a pulsation device to the dental appliance to cause the dental appliance to vibrate;
inserting the dental appliance into the patient's oral cavity;
transmitting vibrations to the patient's dentition through the inserted dental appliance to stabilize the resulting eruption;
applying a biting pressure to the appliance and releasing the biting pressure from the appliance to increase the force and speed of tooth eruption, wherein the transmitting vibrations and applying the biting pressure increase blood circulation to erupted teeth, non-erupted teeth, and muscle surrounding the dental appliance;
applying the biting pressure to the appliance and releasing the biting pressure from the appliance for a predetermined period of time;
wherein the predetermined period of time includes the application of biting pressure for a first predetermined period of time followed by the release of the biting pressure for a second predetermined period of time; and
wherein the first predetermined period of time is substantially 5 minutes and the second predetermined period of time is substantially 1 minute.

4. A method of correcting overbite of a patient comprising:
providing a dental appliance having eruption guidance features, wherein the dental appliance having eruption guidance features includes a shield having a vertical dimension at the front of the shield extending past the patient's gum;
connecting a pulsation device to the dental appliance to cause the dental appliance to vibrate;
inserting the dental appliance into the patient's oral cavity;
transmitting vibrations to the patient's dentition through the inserted dental appliance to stabilize the resulting eruption;
applying a biting pressure to the appliance and releasing the biting pressure from the appliance to increase the force and speed of tooth eruption, wherein the transmitting vibrations and applying the biting pressure increase blood circulation to erupted teeth, non-erupted teeth, and muscle surrounding the dental appliance;
applying the biting pressure to the appliance and releasing the biting pressure from the appliance for a predetermined period of time;
wherein the predetermined period of time includes the application of biting pressure for a first predetermined period of time followed by the release of the biting pressure for a second predetermined period of time; and
wherein the application of biting pressure and the release of biting pressure alternate repeatedly for total time-period of substantially 2 hours per day, wherein the total time-period of substantially two hours per day includes a continuous session of 2 hours or includes two or more separate time-periods per day having a total time-period of 2 hours.

5. The method of claim 4 wherein the first predetermined period of time is substantially 5 minutes and the second predetermined period of time is substantially 1 minute.

* * * * *